United States Patent [19]

Åkerlund

[11] 4,372,302
[45] Feb. 8, 1983

[54] INSTRUMENT FOR RETRIEVAL OF RETRACTED THREADS OF INTRAUTERINE CONTRACEPTIVE DEVICES

[75] Inventor: Mats Åkerlund, Lund, Sweden

[73] Assignee: AB Myometricon, Sweden

[21] Appl. No.: 250,927

[22] Filed: Apr. 6, 1981

[30] Foreign Application Priority Data

Apr. 9, 1980 [SE] Sweden ................................ 8002692

[51] Int. Cl.³ ............................................. A61F 5/46
[52] U.S. Cl. .................................. 128/130; 128/303 R
[58] Field of Search ................................ 128/127–130, 128/303 R, 304, 330, 357, 131, 353

[56] References Cited

U.S. PATENT DOCUMENTS 3,769,980 11/1973 Karman .............................. 128/304
3,771,520 11/1973 Lerner ................................. 128/127
3,789,838 2/1974 Fournier et al. .................... 128/130

Primary Examiner—C. Fred Rosenbaum
Attorney, Agent, or Firm—Lewis H. Eslinger

[57] ABSTRACT

The invention concerns an instrument for retrieval of retracted threads of intrauterine contraceptive devices (IUD), the instrument being characterized by a relatively stiff handle part (1) connected to an archedly curved distal part (2), which has a rounded cross-section, is flexible, and, on its concave surface, is provided with a number of notches at relative distances along the curved distal part (3,4,5) these notches to be used for gripping the threads at the insertion and turning of the instrument within the uterus.

4 Claims, 3 Drawing Figures

U.S. Patent  Feb. 8, 1983  4,372,302
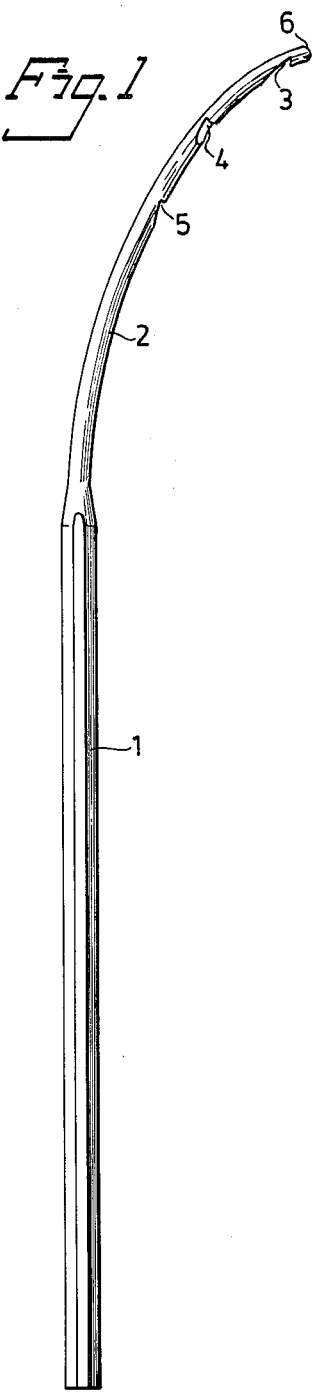
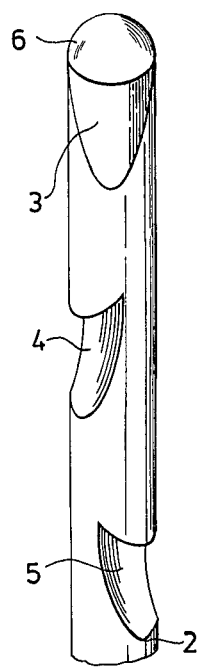
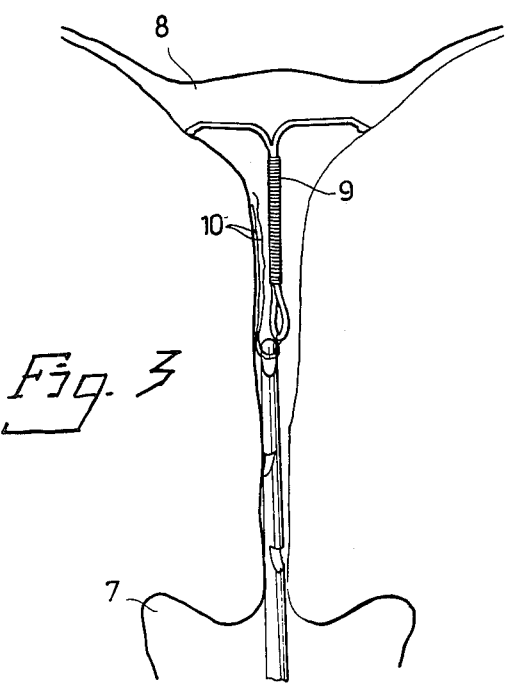

INSTRUMENT FOR RETRIEVAL OF RETRACTED THREADS OF INTRAUTERINE CONTRACEPTIVE DEVICES

The present invention concerns an instrument for retrieval of retracted threads of intrauterine contraceptive devices.

For the prevention of pregnancy a large proportion of fertile women today use intrauterine contraceptive devices (IUD), which are provided with threads hanging out through the cervix, so that the doctor or nurse at a check-up will be able to see that the IUD is still at its place. Many women regularly check themselves that the threads and, thus, the IUD is still in its right place after each menstruation. However, it happens quite frequently that the threads cannot be seen or felt at a check-up which could be due to loss of the IUD, perforation by it of the uterine wall, or retraction of the threads into the uterine cavity. The latter could be the result of enlargement of the uterus due to pregnancy or myomas, but most frequently, retraction of threads occurs without an apparent cause.

By sounding of the uterine cavity one can sometimes verify the presence of an IUD even if the threads are not visible. Another way to verify the correct positioning of an IUD is by x-ray or ultrasonic investigation. The drawbacks of these methods are that an X-ray investigation includes a certain, although small dose of ionizing radiation, and that an ultrasonic investigation is complicated and time-consuming. Furthermore, even if the IUD is found, the question remains how to extract it from the uterus. To leave the IUD with retracted threads would make most women unsure and worried, since they cannot check that the IUD is at place.

One way to retrieve the threads is by means of a forceps, a procedure which may require dilation of the cervix under local or general anesthesia. This method also entails considerable costs (Evans, Obstet. Gynec. 1974:44, 155).

A previous publication discloses the use of a helix-shaped plastic instrument for retrievel of IUD threads (Husemeier and Gordon, Lancet Apr. 14, 1979, p 807). This instrument has the form of a flexible, flat helix, which after washing of the vagina and the cervix should be inserted into the uterine cavity through the cervix canal, during counter-clockwise rotation. Within the uterus the instrument is rotated through 8-10 full circles, which is supposed to wind the threads around the instrument. The threads can then be brought out through the cervix and the IUD be pulled out directly or by gripping the threads with a forceps.

In practical use this helix-shaped instrument has shown several disadvantages. The part of the instrument which has to be inserted through the cervix is so big and has sharp edges which may cause considerable pain. Furthermore it does not function satisfactorily for thread retrieval in a large proportion of the cases. In fact, this instrument was initially designed for the purpose of endometrial curettage, not for retrieving retracted IUD threads.

By the present invention the disadvantages of the known instrument is overcome. The invention concerns in particular an instrument for retrieval of retracted threads of IUDs and is characterized by a relatively stiff handle part connected to an archedly curved distal part which has a rounded cross-section, is flexible, and at its concave surface, is provided with a number of notches at relative distances along the curved distal part, these notches to be used for gripping the threads at the insertion and turning of the instrument within the uterus.

The cross section of the handle part could have any type of shape, but is preferably angular to ensure a safe grip. The distal part which is connected to the handle part has, in relation to the handle part, preferably a smaller cross-section, which preferably is circular or oval. The distal part is furthermore relatively flexible, whereas the handle part is more stiff. The fact that the distal part is archedly curved is an important feature, since thereby the instrument can be more easily adapted to the natural flexion of the uterine wall.

The notches on the concave surface of the distal part can be made by incisions inwards and forwards in the direction of introduction of the instrument. Thereby, notches are produced which do not protrude out of the contour of the distal part. The notches are preferably arranged with axial displacement around the periphery of the distal part.

It is preferable that the notches on the concave surface of the distal part have an acute angle, with the tip of the angle in the direction of introduction of the instrument, i.e. the notches have a front surface in relation to the insertion end, which goes inwards, towards the longitudinal axes of the distal part, and forwards in the direction of insertion of the instrument, and a back surface that meets the front surface in an acute angle. Thereby, a good grip of the threads is achieved when inserting the instrument in the uterus.

The tip of the instrument is preferably rounded.

The instrument can be manufactured from any type of material, but preferably it is made of a medically acceptable plastic material, which is cheap and can be sterilized. If desired the instrument could be strengthened by embedding a metal thread along its length and into the foremost notch. This notch might be modified into a hook to catch the IUD itself. The instrument is best made for non-recurring use and is best provided in throw-away packages.

The invention is described in detail below with reference to the attached drawing, in which FIG. 1 shows the instrument in sectional view and in natural size, FIG. 2 shows a perspective view of the end of the distal part of the instrument in FIG. 1, and FIG. 3 shows schematically in front view the instrument when placed in the uterine cavity (shown schematically in natural size in sectional view).

The instrument according to FIG. 1 is in natural size and consists of a handle part 1, which has an angular cross section in order to enable a safe grip. The handle part 1 is relatively stiff. To the handle part 1 is fitted an archedly curved, in cross section circular, flexible distal part 2, which exhibits a number of notches with acute angles 3, 4, 5 at its concave surface. The distal part 2 has a smaller cross-section than the handle part 1. Furthermore, compared to this the distal part is relatively flexible. As shown in the Figure the notches 3-5 are located at the concave surface of the distal part.

The notches 3, 4, 5 are axially and longitudinally spread around the periphery of the distal part which, furthermore, has a rounded tip 6. The foremost notch 3 is placed near the tip of the instrument and has its incision surface corresponding to the maximal concavity of the instrument. Hereby one can even reach threads, which are located at the very depth of the uterine cavity.

FIG. 2 shows the foremost part of the distal end in detail and enlarged, the reference numbers having the same meaning as in FIG. 1.

FIG. 3 shows the use of the instrument according to the present invention. Upon sterilization of the vagina and cervix by washing, the instrument is introduced through the cervical canal into the uterine cavity 8, where an IUD 9 is located. Since the distal part of the instrument is archedly curved one can by slight turning of the curved distal part adopt it to the flexed uterine wall. By slowly retracting the instrument from the uterus and simultaneously pressing the concave surface of the curved distal part of the instrument against the wall of the uterine cavity, the notches will grip the retracted IUD threads 10, whereby the threads can easily be brought down through the cervical canal into the vagina. There are threads can be seen or felt and thus the right positioning of the IUD can be verified. If desired, the IUD can thereafter be removed from the uterus by pulling of the threads.

I claim:

1. An instrument for retrieval of retracted threads of an intrauterine device within a uterus, comprising a relatively stiff handle and a flexible distal part integral therewith, said distal part having a rounded cross-section and being provided with a plurality of notches spaced along its length for gripping the retracted threads during insertion and turning of the instrument within the uterus, wherein the improvement comprises that the distal part is curved so as to form a concave surface and that the notches are provided on said concave surface of said curved distal part.

2. An instrument according to claim 1, wherein the notches are arranged at an acute angle with each notch having sides which form the angle and which sides converge in the direction of introduction of the instrument.

3. An instrument according to claim 1 or 2, wherein the notches are angulary displaced about the curved distal part and displaced along the longitudinal axis of the curved distal part.

4. An instrument according to claims 2, 3 or 1, wherein the distal part has a rounded tip.

* * * * *